United States Patent
Giurgiutiu

(10) Patent No.: US 7,024,315 B2
(45) Date of Patent: Apr. 4, 2006

(54) IN-SITU STRUCTURAL HEALTH MONITORING, DIAGNOSTICS AND PROGNOSTICS SYSTEM UTILIZING THIN PIEZOELECTRIC SENSORS

(75) Inventor: Victor Giurgiutiu, Columbia, SC (US)

(73) Assignee: University of South Carolina, Columbia, SC (US)

(*) Notice: Subject to any disclaimer, the term of this patent is extended or adjusted under 35 U.S.C. 154(b) by 0 days.

(21) Appl. No.: 10/072,644

(22) Filed: Feb. 8, 2002

(65) Prior Publication Data

US 2003/0009300 A1 Jan. 9, 2003

Related U.S. Application Data

(60) Provisional application No. 60/267,650, filed on Feb. 8, 2001.

(51) Int. Cl.
*G01B 3/00* (2006.01)

(52) U.S. Cl. .................. 702/33; 702/34; 702/35; 702/36

(58) Field of Classification Search ............. 702/35, 702/36, 33, 34; 73/626, 627, 632, 862.4
See application file for complete search history.

(56) References Cited

U.S. PATENT DOCUMENTS

| | | | |
|---|---|---|---|
| 3,713,127 A | 1/1973 | Keledy et al. | 340/261 |
| 4,821,575 A | 4/1989 | Fujikake et al. | 73/626 |
| 4,995,260 A | 2/1991 | Deason et al. | 73/632 |
| 5,167,157 A | 12/1992 | Wertz et al. | 73/627 |
| 5,814,729 A | 9/1998 | Wu et al. | 73/588 |
| 6,006,163 A | 12/1999 | Lichtenwalner et al. | 702/36 |
| 6,370,964 B1* | 4/2002 | Chang et al. | 73/862.046 |
| 2001/0047691 A1* | 12/2001 | Dzenis | 73/587 |

* cited by examiner

*Primary Examiner*—Kamini Shah
(74) *Attorney, Agent, or Firm*—Nelson Mullins Riley & Scarborough LLP

(57) ABSTRACT

A method of detecting a damaged feature within a structure includes embedding a plurality of thin piezoelectric ceramic sensors on the structure. A first sensor is excited so that the first sensor produces a responsive signal in the structure. The responsive signal is received at a second sensor. The presence or absence in the received responsive signal of at least one predetermined signal characteristic is determined, where the predetermined signal characteristic is related to existence of the damage feature.

22 Claims, 10 Drawing Sheets

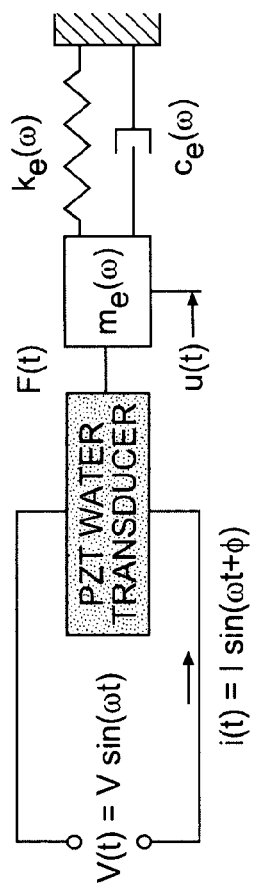
FIG. 6
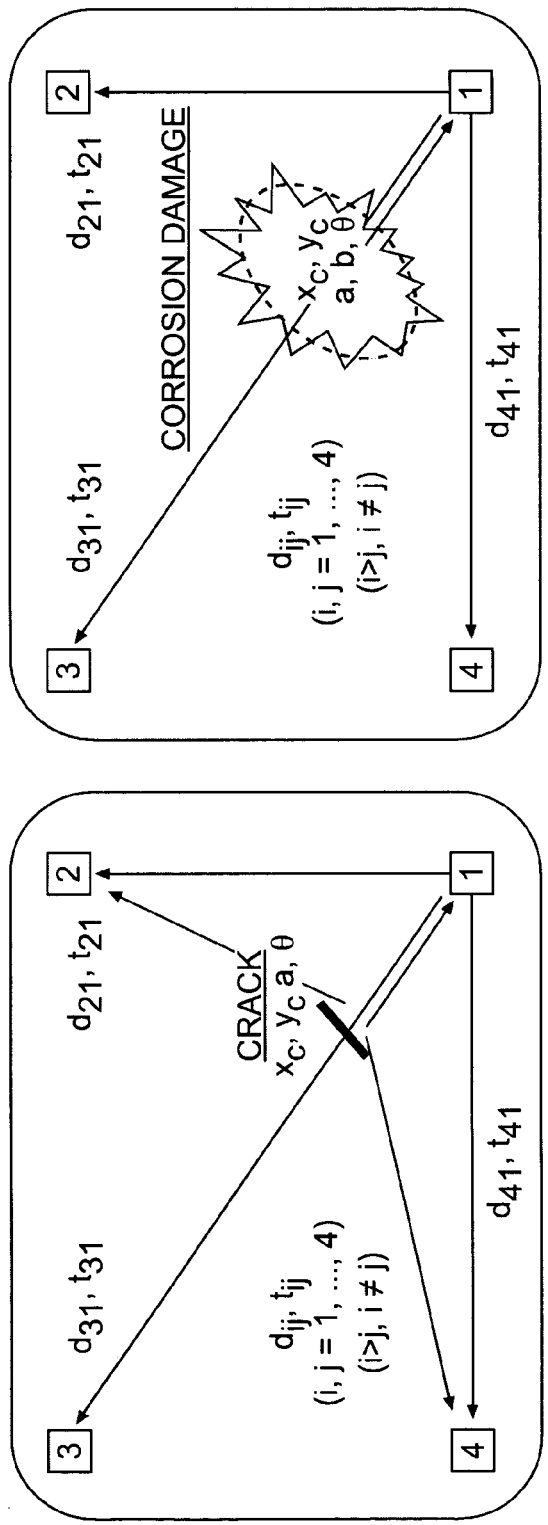
FIG. 7a
FIG. 7b

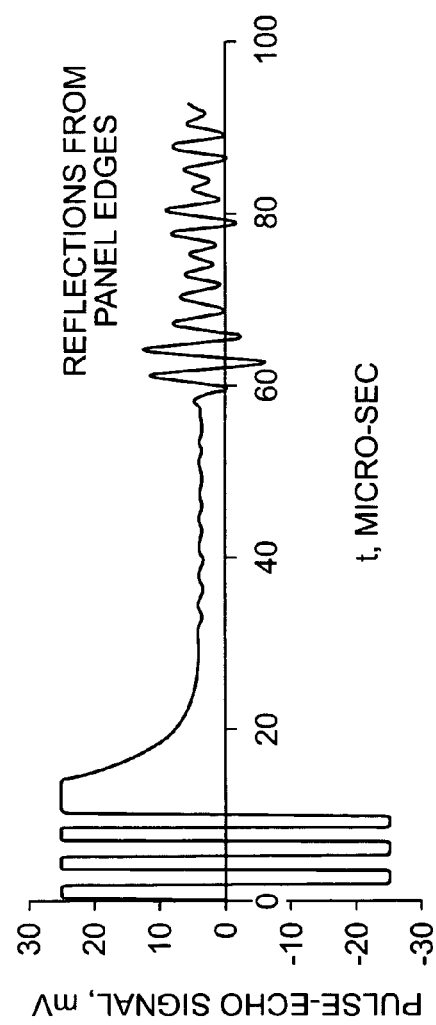
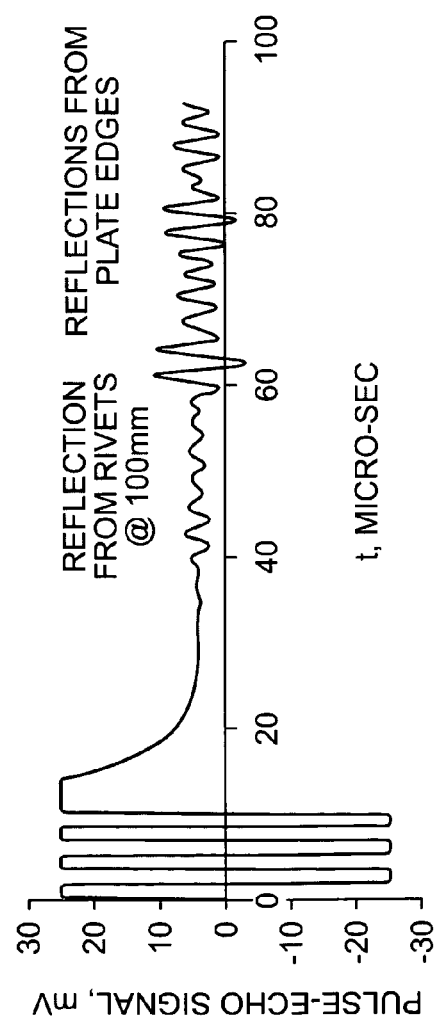

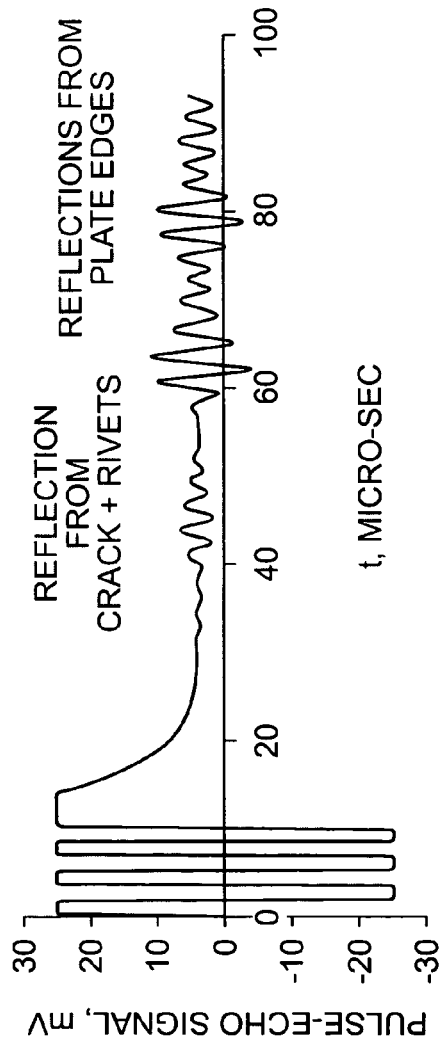
FIG. 10c
FIG. 10d
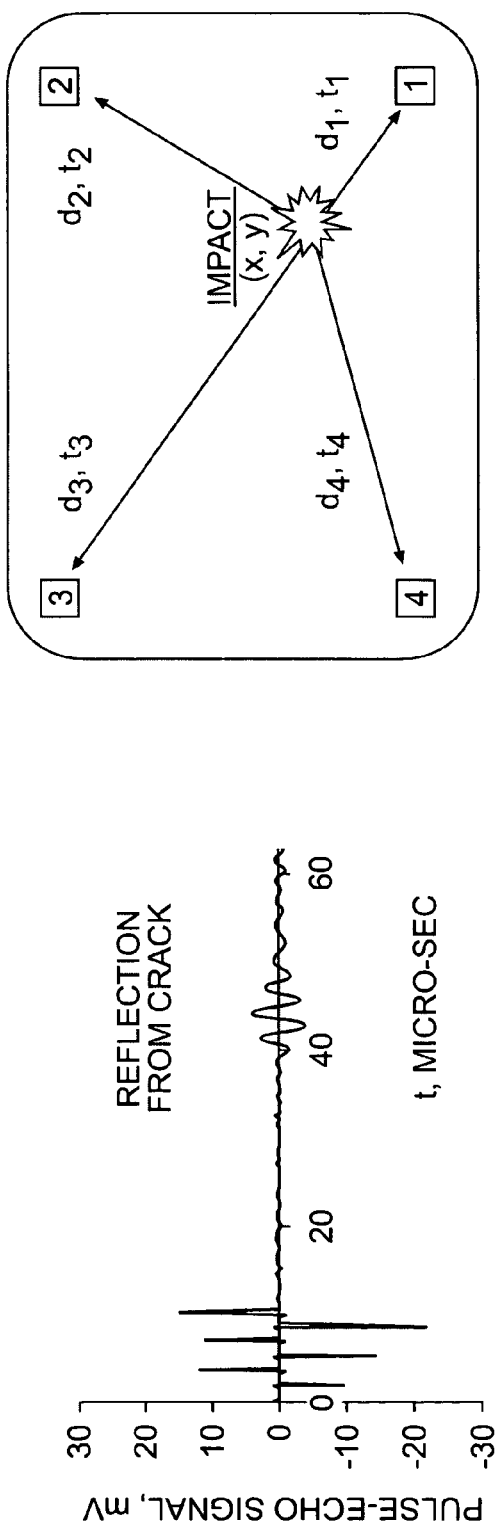
FIG. 11

IN-SITU STRUCTURAL HEALTH MONITORING, DIAGNOSTICS AND PROGNOSTICS SYSTEM UTILIZING THIN PIEZOELECTRIC SENSORS

This application claims the benefit of U.S. Provisional Application No. 60/267,650, filed Feb. 8, 2001 and entitled "In-situ Structural Health Monitoring, Diagnostics and Prognostics System Utilizing Smart Active Sensors with Embedded Intelligence and Wireless Installation," the entire disclosure of which is incorporated by reference herein.

BACKGROUND OF THE INVENTION

It has been recognized that there is a need to monitor the existence and effects of damage and corrosion in structural materials. Aircraft components provide a much publicized example, but the need exists in a variety of other structures, for example pipelines and building members. To detect defects, traditional modal analysis testing generally relies on structural excitation and vibration pickups. Structural excitation methods, in turn, usually employ either harmonic sweep or impulse excitation. The former method is more precise and can focus on resonant frequencies, while the latter is more expedient. Vibration pickups can measure displacement, velocity or acceleration. The use of self-conditioning accelerometers and laser velocimeters are known. Accelerometers allow installation of sensor arrays that accurately and efficiently measure mode shapes, while lasers offer contactless measurements that are effective for low mass sensitive structures.

In general, it is known to propagate electromagnetic signals through materials in order to measure anomalies in the materials. Ultrasonic transducers, for example, include piezoelectric crystals of a certain mass. The crystals are excited at a known resonant frequency so that the resonant crystal vibration generates an ultrasonic signal. Ultrasonic sensors, which are relatively bulky and expensive, are typically used in portable devices placed in communication with the structure of interest so that the crystals propagate ultrasonic waves into the material. Sensors detecting resulting signals in the material sense patterns that indicate anomalies in the materials such as cracks or corrosion.

SUMMARY OF THE INVENTION

It is an object of the present invention to provide an in-situ sensor system for structural material analysis.

This and other objects may be achieved within a method of detecting a damage feature in a structure.

A plurality of thin piezoelectric ceramic sensors are embedded on the structure. A first sensor is excited so that the first sensor produces a responsive signal in the structure. The responsive signal is received by a second sensor, and the presence or absence of at least one predetermined signal characteristic in the received responsive signal is determined. The predetermined signal characteristic is related to existence of the damage feature.

The accompanying drawings, which are incorporated in and constitute a part of this specification, illustrate one or more embodiments of the invention and, together with the description, serve to explain the principles of the invention.

BRIEF DESCRIPTION OF THE DRAWINGS

A full and enabling disclosure of the present invention, including the best mode thereof directed to one of ordinary skill in the art, is set forth in the present specification, which makes reference to the appended drawings, in which:

FIG. 6 is an electrical schematic view of a sensor in accordance with an embodiment of the present invention;

FIGS. 7a and 7b are schematic illustrations of a sensor array in accordance with an embodiment of the present invention;

FIGS. 10a–10d are graphical illustrations of measurement and response signals resulting from use of a transducer in accordance with an embodiment of the present invention;

FIG. 11 is a schematic illustration of a sensor array in accordance with an embodiment of the present invention in passive detection mode.

Figure 1:
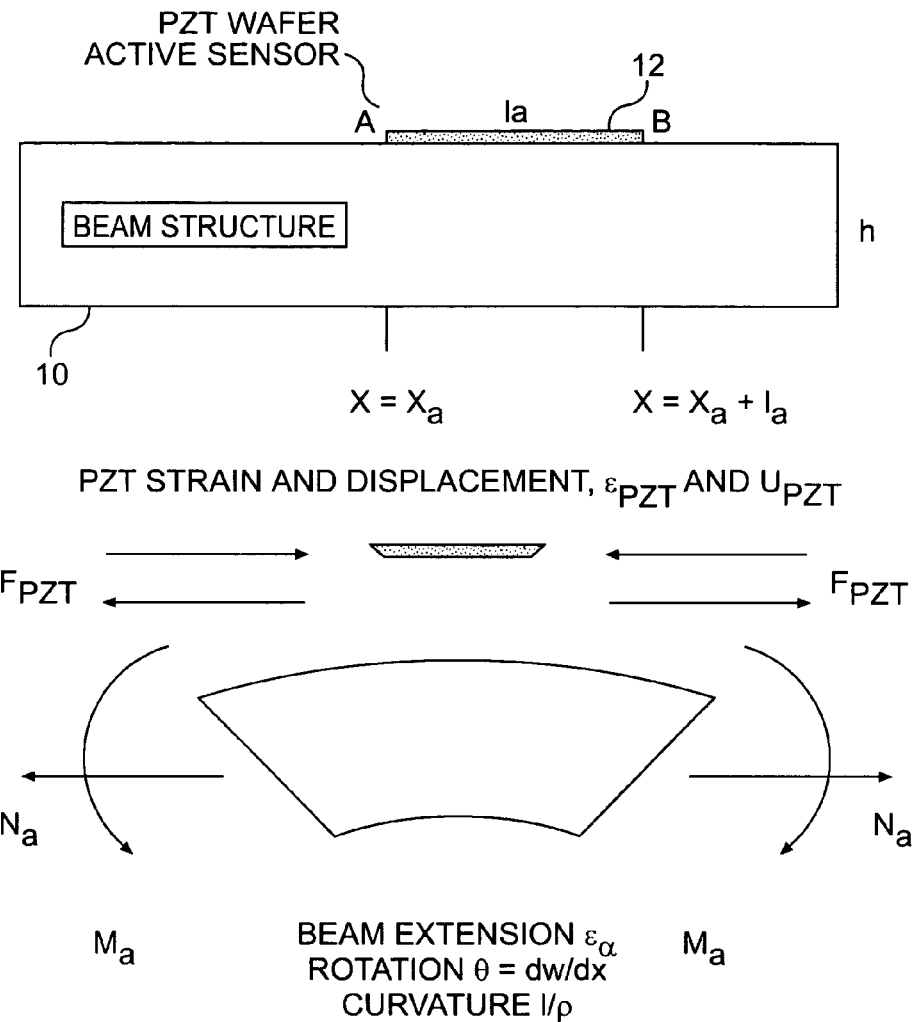
FIG. 1 is a cross-sectional schematic view of a thin piezoelectric sensor embedded on a structure for in-situ measurement in accordance with an embodiment of the present invention.

Repeat use of reference characters in the present specification and drawings is intended to represent same or analogous features or elements of the invention.

DETAILED DESCRIPTION OF PREFERRED EMBODIMENTS

Reference will now be made in detail to presently preferred embodiments of the invention, one or more examples of which are illustrated in the accompanying drawings. Each example is provided by way of explanation of the invention, not limitation of the invention. In fact, it will be apparent to those skilled in the art that modifications and variations can be made in the present invention without departing from the scope or spirit thereof. For instance, features illustrated or described as part of one embodiment may be used on another embodiment to yield a still further embodiment. Thus, it is intended that the present invention covers such modifications and variations as come within the scope of the appended claims and their equivalents.

Generally, the present invention relates to embedding relatively small transducers on a structure in order to monitor the structure's structural health. Several examples are provided, namely, active electromechanical impedance sensing, active ultrasonic sensing, and passive sensing through interrogation of acoustic emissions and detection of elastic waves indicating impacts by a foreign body. A description of an electromechanical (E/M) impedance damage identification strategy is presented in the Appendix. Summarizing the identification strategy, the effect of a piezoelectric active sensor affixed to a structure is to apply a local strain parallel to the structure's surface that creates stationary elastic waves in the structure. The structure presents to the active sensor the drive-point impedance, $Z_{str}(\omega)=i\omega m_e(\omega)+c_e(\omega)-ik_e(\omega)/\omega$. Through the mechanical coupling between the PZT active sensor and the host structure, on one hand, and through the electro-mechanical transductance within the PZT active sensor, on the other hand, the drive-point structural impedance is directly reflected into the effective electrical impedance as seen at the active sensor terminals, as shown in FIG. 6. The apparent electro-mechanical impedance of the piezo-active sensor as coupled to the host structure is:

$$Z(\omega) = \left[i\omega C\left(1 - \kappa_{31}^2 \frac{Z_{str}(\omega)}{Z_{PZT}(\omega) + Z_{str}(\omega)}\right)\right]^{-1}$$

Where $Z(\omega)$ is the equivalent electro-mechanical admittance as seen at the PZT active sensor terminals, C is the zero-load capacitance of the PZT active sensors, $K_{31}$ is the electro-mechanical cross coupling coefficient of the PZT active sensor ($K_{31}=d_{13}/\sqrt{s_{11}\bar{\epsilon}_{33}}$), $Z_{str}$ is the impedance of the structure, and $Z_{PZT}$ is the impedance of PZT active sensor.

The electromechanical impedance method is applied by scanning a predetermined frequency range in the hundreds of kHz band and recording the complex impedance spectrum. By comparing the impedance spectra taken at various times during the service life of a structure, structural degradation and the appearance of incipient damage may be identified. The frequency should be high enough, however, that the signal wavelength is significantly smaller than the defect size.

Figure 5:
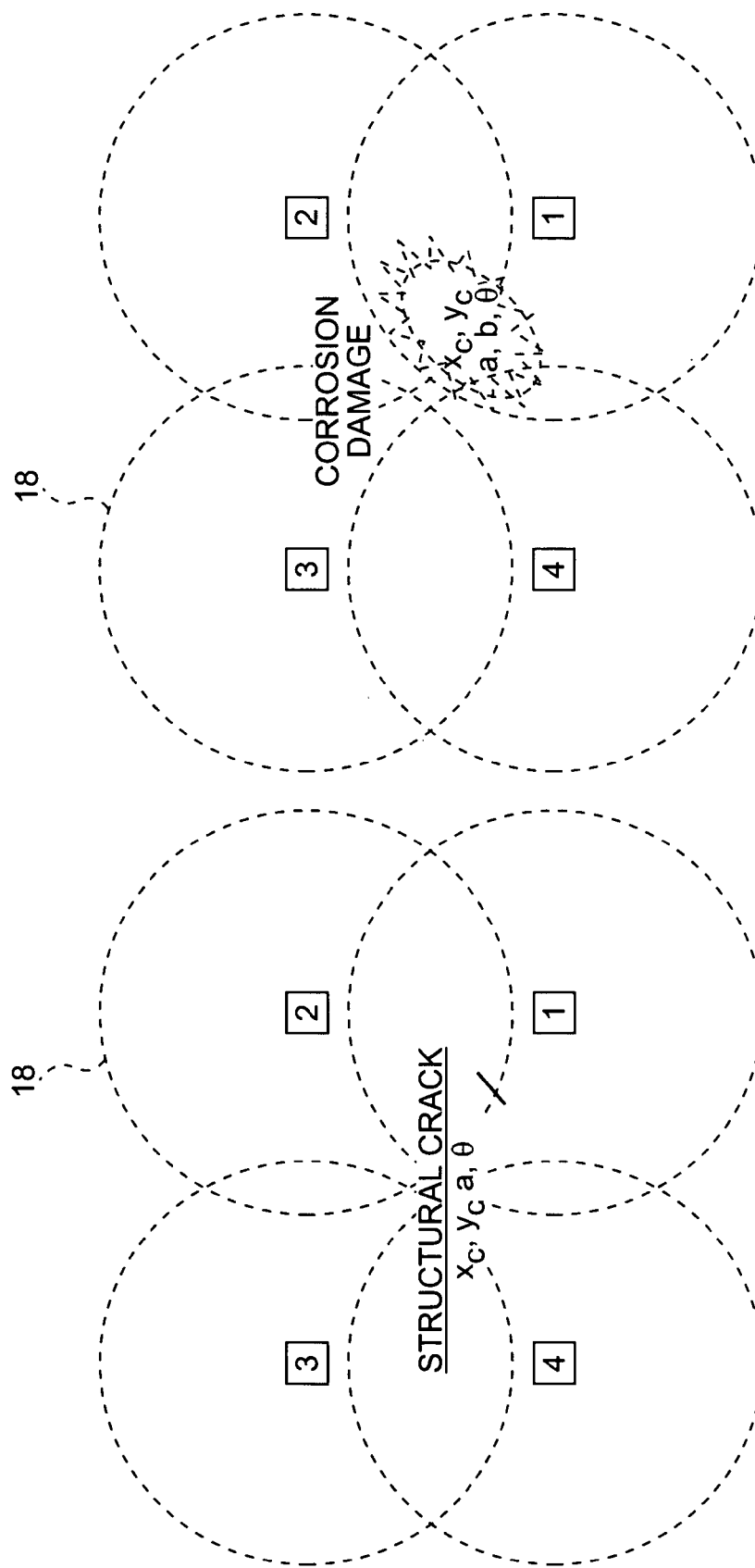
FIGS. 5a and 5b are schematic illustrations of a sensor array in accordance with an embodiment of the present invention.

Referring to FIGS. 5a and 5b, consider an array of four active sensors. Each active sensor has its own sensing area characterized by a sensing radius and the corresponding sensing circles indicated at 18. Inside each sensing area, the sensor detection capability diminishes with the distance between the sensor and the damaged or corroded area. A damage feature that is placed in the sensor near field is expected to create a larger disturbance in the sensor response than a damage feature placed in the far field. Effective area coverage is insured when the sensing circles of several sensors overlap. The diagnostics of the adjacent structure is performed using the active (real) part of the E/M impedance. Incipient damage changes taking place in the structure are reflected in the drive-point structural impedance. The change in the structural drive-point impedance extensively affects the real part of the effective electromechanical impedance of the piezoelectric active sensor embedded on the structure.

FIG. 5a illustrates a structural crack placed in the sensing circle of the first active sensor. The presence of the crack modifies the structural field and effective drive-point structural impedance as seen by that sensor. At the same time, the crack also belongs to the sensing circle of the second sensor, but it is at the periphery of this circle. Thus, it is expected that the effective drive-point structural impedance as seen by the second sensor will also be affected but to a much lesser extent than that of the first sensor. The structural crack is outside the sensing circles of the third and fourth sensors, and their drive-point structural impedances will be almost unchanged. By virtue of the impedance equation above, changes in the drive-point structural impedance are directly reflected in the sensor's E/M impedance. Thus, the crack illustrated in FIG. 5a is expected to strongly modify the E/M impedance of the first sensor, to slightly modify that of the second sensor and to leave the E/M impedances of the third and fourth sensors unchanged.

FIG. 5b illustrates a patch of corrosion damage placed in the sensing circle of the first active sensor. The corrosion damage also belongs, to a lesser extent, to the sensing circles of the second and fourth sensors. The effective drive-point structural impedance seen by the first sensor will be strongly modified. The drive-point impedance seen by the second sensor will be modified to a lesser extent, and the impedance of the fourth sensor will be slightly modified. The drive-point impedance of the third sensor remains virtually unchanged. As indicated by the impedance equation above, these changes in drive-point structural impedance will be directly reflected in the sensors' E/M impedances. Thus, the corrosion damage strongly modifies the E/M impedance of the first sensor, somewhat modifies the E/M impedance of the second sensor, slightly modifies the E/M impedance of the fourth sensor and leaves the E/M impedance of the third sensor unchanged.

The discussion above focuses on the use of E/M impedance sensing to detect defect or damage features in a structure. It is also possible to use active piezoelectric sensors to propagate elastic waves through the structure so that signal reflections and scattering effects may be used to detect damage features such as cracks and corroded areas. Although it should be understood that the present method may include the use of a single sensor, the embodiment described herein includes the use of a sensor array. In general, the sensors in a given array are clustered in a predetermined positional arrangement and are sequentially excited in round-robin fashion so that each sensor emits an ultrasonic acoustic wave into the structure. The remaining sensors in the array, as well as the originating sensor, monitor the emitted signals and, from the received responses, may determine the existence and position of a damage feature. Excitation may be at a fixed frequency, a frequency burst or a frequency sweep. The particular frequency band may be selected consistently with the size of the feature to be identified.

FIGS. 7a and 7b, illustrate an array of four active sensors in an ultrasonic sensing mode. Piezoelectric active sensors can act as both sensors and actuators. At each measurement, one of the four active sensors is both an actuator and a sensor, while the remaining three act only as sensors. The actuator function moves round-robin among the four sensors. Assuming the first sensor is the actuator, it generates elastic waves that propagate through the material and are sensed at the second, third and fourth active sensors. The properties of these waves are affected by the presence of impact damage or material defects and can be interpreted to yield damage location and amplitude. This method can be applied, for example, to detect damage arising from cracks and corrosion.

Referring to FIG. 7a, it is desirable to characterize crack damage in terms of its location ($x_c$, $y_c$), its size and its orientation ($a, \theta$). When a crack is present in the wave path, a signal generated by the actuator piezoelectric sensor will be deflected, reflected and transmitted at the crack. The relative proportions among deflection, reflection and transmission vary with damage, size and orientation. In FIG. 7a, the second and fourth active sensors receive both direct and deflected wave signals from the actuator (i.e. the first active sensor). The first sensor also acts as a receptor and detects a wave reflected from the crack. The third active sensor receives a transmitted wave having an amplitude that is a function of the damage size. Thus, a matrix of information in terms of event arrival time and amplitude may be determined from the information detected by the four sensors when the first sensor is the actuator. Thereafter, a round-robin procedure is imposed in which the second, third, and fourth sensors in turn become the actuators An information matrix is obtained at each such measurement. The damage, location, size and orientation may be derived using conventional linear algebra or neural network algorithms. Generally, the use of multiple round-robin measurements provides more information than needed. This over-specification, however, mitigates data error.

FIG. 7b illustrates a corrosion damage example. Corrosion damage is multi-dimensional and can cover a wide area. In the example shown in FIG. 7b, the first active sensor generates elastic waves that propagate through the material and are sensed at the second, third, and fourth sensors. The damaged material affects the speed and attenuation of the waves. As with crack damage, it is desirable to characterize corrosion damage in terms of location, size and orientation. Orientation may be defined in any suitable manner, for example the major and minor axes of a damage ellipse and axis inclination. In the example, elastic waves received by the second and fourth sensors do not engage the corroded area and are, therefore, unaffected. Waves received by the third sensor travel through the damaged material and are therefore modified in speed and attenuation. The material degradation may be so advanced that no detectable waves are received at the third sensor. As each of the four sensors emits elastic waves in round-robin fashion, an information matrix is stored so that the location, size and orientation of the damaged area are determined. Again, the solution may be derived from conventional linear algebra solutions or neural networks, and the use of multiple measurements mitigates errors.

Figure 8B:
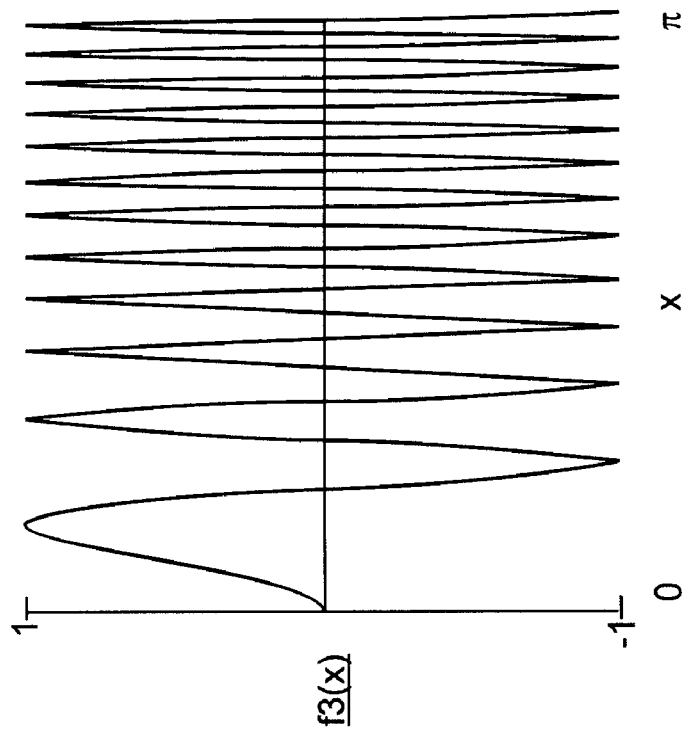
FIGS. 8a–8d are graphical illustrations of elastic measurement waves generated by a transducer array in accordance with an embodiment of the present invention.
Figure 8A:
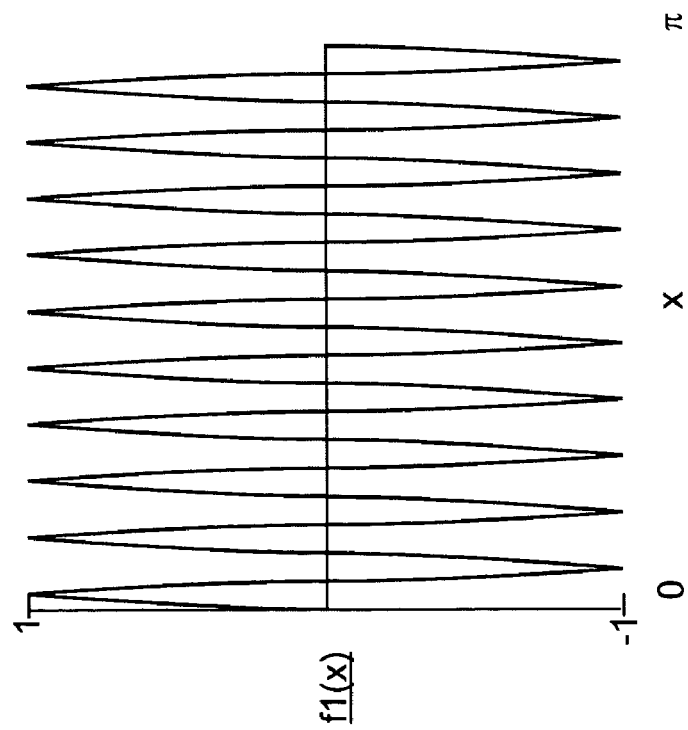
Figure 8D:
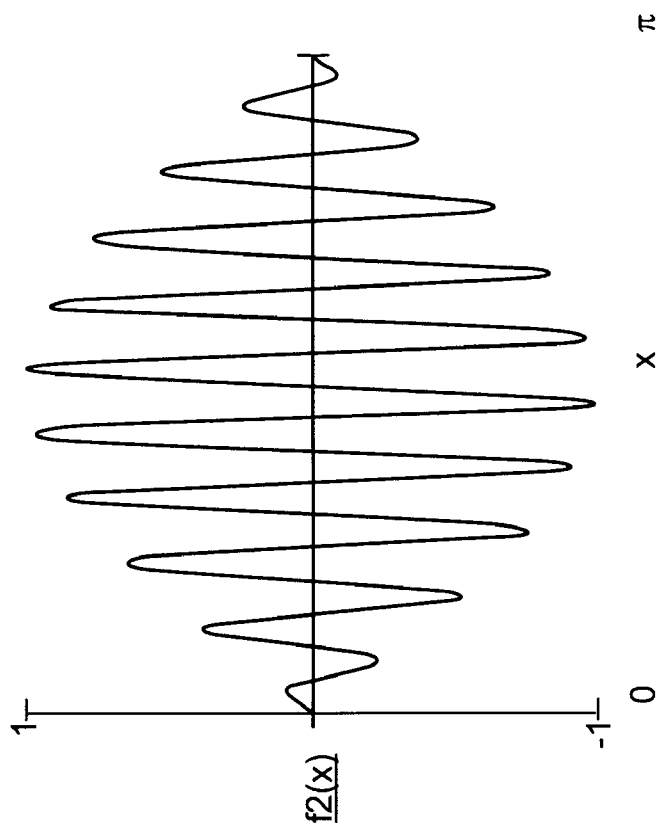
Figure 8C:
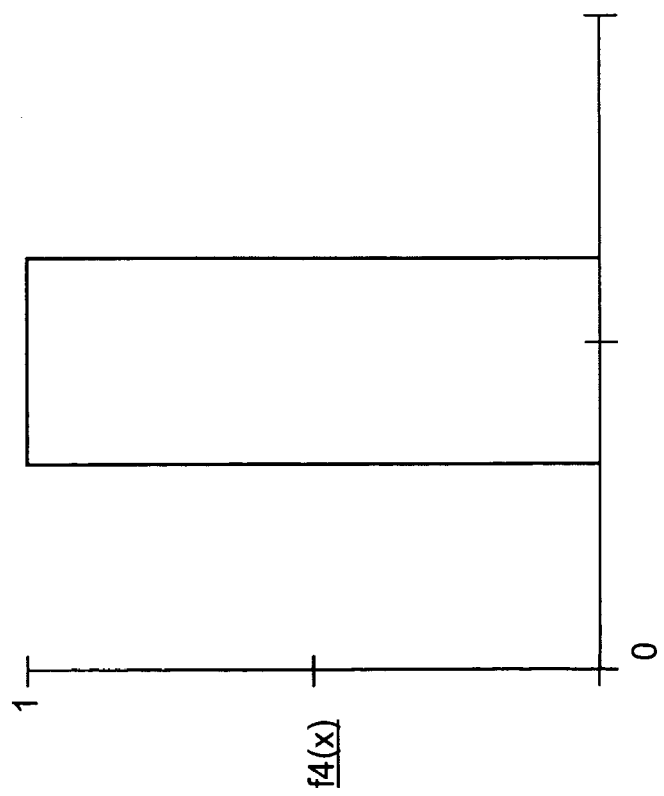

The types of elastic waves used in the damage identification process may vary, for example among constant amplitude sine waves, bursts, sweeps and impulses. Four wave-type examples are provided in FIGS. 8a–8d. The constant amplitude sine wave in FIG. 8a is the simplest waveform. Because excitation frequency should be matched with the structural characteristics of the damage area in order to excite a structural resonance, however, use of the constant amplitude wave may require multiple emissions at varying frequencies to test for all damage types of interest. Accordingly, a frequency sweep as in FIG. 8b may be desirable in that it permits the excitation of more than one frequency in the same measurement. An impulse signal as in FIG. 8c permits the excitation of a wide frequency spectrum. A frequency burst as in FIG. 8d may be desirable in that it includes a dominant frequency that can be tuned to particular structural and flaw-size requirements. Since its frequency content is known, a burst wave can be readily detected and filtered from background noise, and its limited duration facilitates the identification and analysis of burst reflection from defects and boundaries.

Experimental Results

Figure 9A:
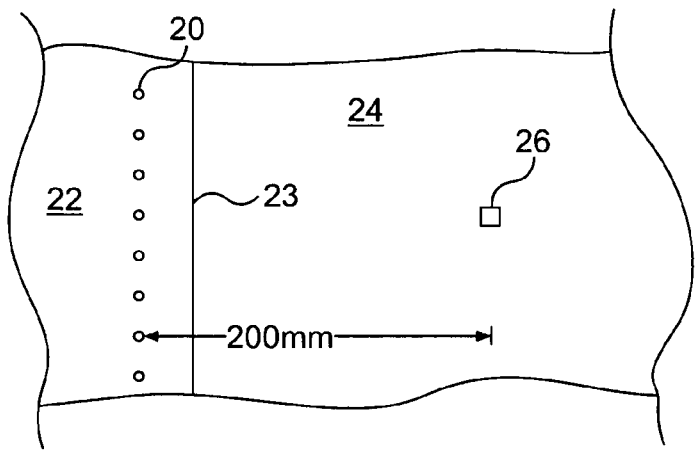
FIGS. 9a–9c are schematic illustrations of embedded sensors in accordance with an embodiment of the present invention.
Figure 9B:
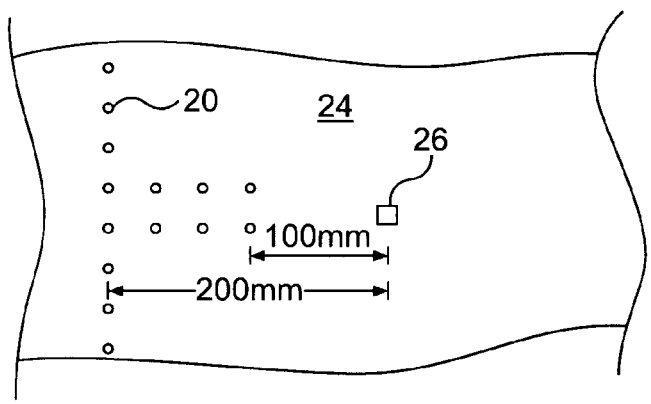
Figure 9C:
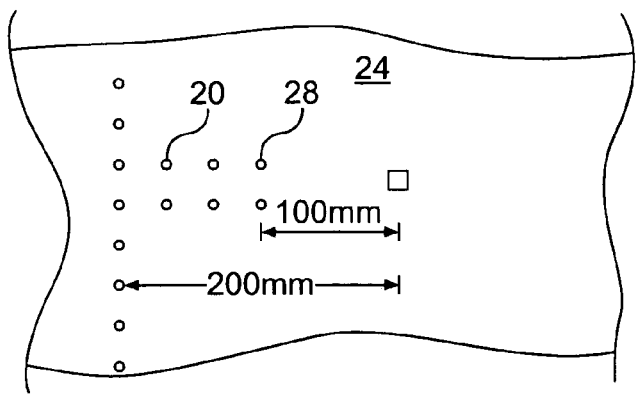

Lamb-wave propagation experiments were conducted on aging aircraft panels using a number of PZT active sensors affixed at various locations. Experiments were performed to verify the wave propagation properties and to identify reflections due to intrinsic construction features of the panels, for example, rivets, splice joints, etc. The illustrations in FIGS. 9a–9c provide a crack detection example. Referring to FIG. 9a, a series of rivets 20 attach to panel sections 22 and 24 so that a side edge 23 of panel 24 faces toward the right in the view shown in FIG. 9a. A piezoelectric active sensor 26 is attached by adhesive to panel 24 at a distance of 200 mm from rivets 20. A more complicated array of rivets is provided on panel 24 in FIG. 9b. The panel shown in FIG. 9c includes the same rivet arrangement, with the addition of a simulated crack (12.75 mm EDM hairline slit) 28 starting from the right-most rivet at the top horizontal row. That is, FIG. 9c illustrates the damaged panel. Experiments were also conducted on a panel (not shown) having no rivets or cracks.

In the clear panel (not shown) and the panels of FIGS. 9b and 9c, PZT sensors 26 emitted an approximately 25 mV continuous frequency wave. FIG. 10a shows the emitted and received signals on the undamaged panel without rivets (not shown). The graph shows the emitted signal, centered at around 5.3 micro-seconds, and multiple reflections from the panel edges. The reflections start to arrive at approximately 60 micro-seconds. FIG. 10b illustrates the signals for the panel shown in FIG. 9b. The signal features reflection from the rivets and multiple reflections from the panel edges. The reflection from the rivets arrives at approximately 42 micro-seconds, indicating an approximate time-of-flight having the value TOF=37 micro-seconds. This TOF is consistent with traveling 200 mm at a group velocity of approximately 5.4 km/s. FIG. 10c shows the signal recorded on the damaged panel of FIG. 9c. The signal response is similar to that shown in FIG. 10b, but is stronger at the 42 micro-second position. Subtracting the signal of FIG. 10b from that of FIG. 10c, as shown in FIG. 10d, identifies the effect of the crack. That is, the strong wave pack centered on 42 micro-seconds illustrates the response from the crack.

Accordingly, where an array of sensors is disposed on or in a panel, and where signals are initially measured in the undamaged structure to obtain baseline measurements, the baseline measurements may be subtracted from subsequent measurements to identify the existence of damage features. The time-of-flight determines the distance from the respective sensor. By measuring distances from multiple sensors in the array, the location of a damage feature with respect to the sensors may be determined. Moreover, the use of multiple measurements, sequentially activating the individual sensors in the array in round-robin fashion, provide for precise location.

The examples provided above, i.e., impedance sensing and ultrasonic sensing, rely on active sensors to measure structural characteristics. The present invention may also, however, be used in passive modes to detect structural damage. In certain of these embodiments, a plurality of sensors is disposed in a predetermined orientation relative to each other and at known positions on the structure. The sensor outputs are monitored intermittently or continuously, even though the sensors may not be engaged in either of the active measurement procedures described above. Damage events may be identified through the recept-ion of stress wave-s generated in the structure through impacts or other material disruptions. Certain waves may, for example, indicate an occurrence of a low-velocity impact. The sensor may also, however, detect acoustic emission signals that indicate damage has occurred. By determining and recording the location and time of damage events, a record may be compiled to predict the structure's remaining operative life.

FIG. 11 illustrates a damage event taking place in a zone monitored by four piezoelectric transducers acting as passive sensors. In this example, the damage under consideration is a low-velocity impact. The impact location and intensity are determined from elastic wave signals received by the four sensors. The arrival time at each sensor is proportional to the distance between the sensor and the impact location.

Accordingly, a simple triangulation is used to determine the impact's position with respect to the sensors. This information is provided to a computer (not shown) that time-stamps the information so that a damage event record is kept. With four sensors, more data is available than necessary. Thus, an optimal solution algorithm, for example least squares, is used. Damage intensity is determined simultaneously by inclusion in the variable list. A neural network algorithm may be applied instead of explicit calculation.

Information-rich data received from the sensors is preferably processed such that only relevant content is retained. The elimination of spurious noise and far-field disturbances, and the identification of useful information directly related to structural damage, is addressed through appropriate signal processing methodologies. Mathematically, the determination of the structure's physical condition using sensor measurements is a nonlinear inverse problem. Signal processing and interpretation methods may be application-specific (model-based) or generic (non-model). Conventional (for example, Fourier analysis) and advanced (for example, Wavelet analysis and digital filters) algorithms available in specialized software packages (for example, MATLAB, LABVIEW, MATHCAD, or AUTOSIGNAL) may be used, as well as neural networks and expert systems.

In operation, transducers in a measurement array execute self-diagnostics (as described in the Appendix) prior to damage detection measurement cycles. Temperature and humidity are the primary environmental changes that affect sensor calibration. Generally, these changes may affect the sensor itself and/or its adhesive interface with the structure. Although the values of the piezoelectric coefficients vary with temperature, the general aspect of the frequency response curve is only shifted. Thus, by calibrating the frequency shift over a variety of temperatures, the system may compensate for temperature changes, thereby maintaining the general nature of the E/M impedance spectrum. The sensor/structure adhesion may be affected by both humidity and temperature, and the combination of humidity and temperature change may be especially detrimental to the adhesive interface. Thus, the self-diagnostic described in the Appendix with respect to FIG. 3 may be employed to identify disbanded sensors.

Each sensor may be formed as a small square or disk of thin piezoelectric ceramic material. In one embodiment, the length and width of each wafer is less than 13 mm, +/−0.13 mm, and between 0.2 mm and 0.49 mm thick, +/−0.025 mm, respectively. Electrodes are attached to the sensors, which communicate with a personal computer, other computing devices and/or other system components, through hard-wire or wireless connections. Sensors may be embedded on structures by, for example, insertion into a composite material during the layering process so that the sensor is actually within the structure or by adhesive attachment to the structure's outer surface as discussed above.

Figure 12:
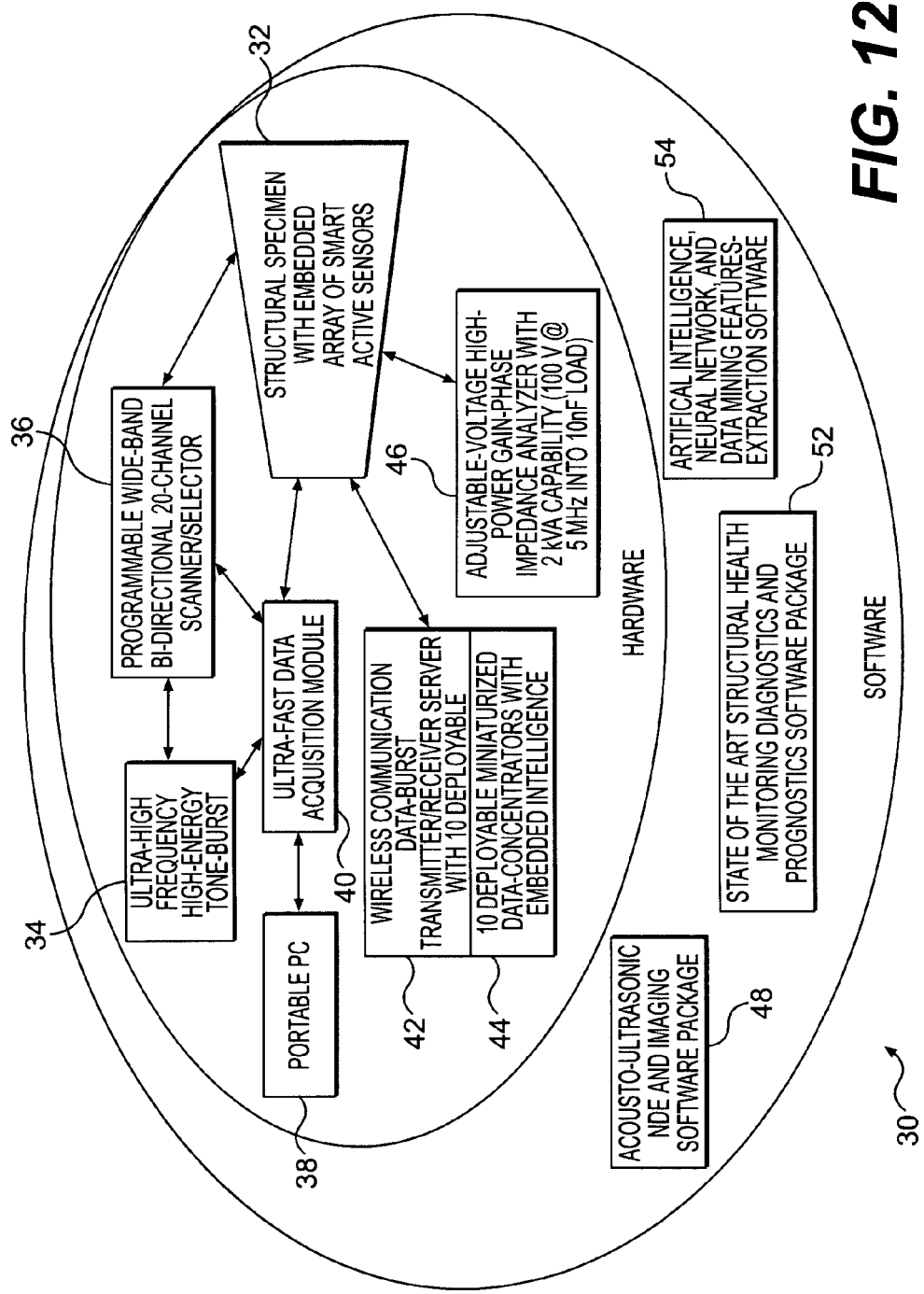
FIG. 12 is a block diagram illustration of a sensor and monitoring system in accordance with one or more embodiments of the present invention.

FIG. 12 provides an overview of an embodiment of the present invention. System 30 includes one or more structures 32 having one or more transducer arrays disposed thereon as described above. For ultrasonic acoustic wave sensing, an ultra-high frequency high-energy tone-burst source 34 excites individual sensors within each transducer array in round-robin fashion through a programmable wideband bi-directional twenty-channel scanner/selector 36. These components communicate with a personal computer 38 through an ultra-fast data acquisition module 40. Computer 38 also acquires measurement data from the transducer array through data acquisition module 40.

In wireless applications, the system may include a wireless communication data-burst transmitter/receiver server 42 that excites and reads the transducer array through a plurality of data-concentrators 44. That is, assuming there are a plurality of transducer arrays disposed about a structure, each transducer is attached to an antenna that communicates with a data-concentrator 44 dedicated to the transducer's array. The one or more data-concentrators communicate with transmitter/receiver server 42 which, in turn, wirelessly communicates with an antenna associated with computer 38 or acquisition module 40.

For impedance sensing, an adjustable-voltage-power gain-phase impedance analyzer 46 excites the transducers, which output measurement information back to analyzer 46. Analyzer 46 includes software algorithms to analyze the sensor data to determine the locations and orientation of damage features as described above. Alternatively, analyzer 46 may forward the data to computer 38 for analysis. Generally, computer 38 houses the system's software components, the operation of which is generally described above and which may include non-destructive evaluation and imaging software package 48, monitoring diagnostics and analysis software package 52 and/or artificial intelligence, neural-network and data mining software 54.

While one or more preferred embodiments of the invention have been described above, it should be understood that any and all equivalent realizations of the present invention are included within the scope and spirit thereof. The embodiments depicted are presented by example only and are not intended as limitations upon the present invention. Thus, it should be understood by those of ordinary skill in this art that the present invention is not limited to these embodiments since modifications can be made. Therefore, it is contemplated that any and all such embodiments are included in the present invention as may fall within the literal or equivalent scope of the appended claims.

APPENDIX

Because of their intrinsic electro-mechanical (E/M) coupling, commercially available low-cost piezoceramics can be used as both sensors and actuators. The frequency bandwidth of these devices is orders of magnitude larger than that of conventional shakers and impact hammers. Small piezoelectric ceramic wafers can be permanently attached to structural surfaces to form sensor and actuator arrays that permit effective modal identification in a wide frequency band. Assuming a single degree of freedom, the electrical admittance, as measured at the terminals of the piezoelectric (PZT) wafer attached to a structure, is as follows:

$$Y(\omega) = i\omega C\left(1 - \kappa_{31}^2 \frac{Z_{str}(\omega)}{Z_{str}(\omega) + Z_A(\omega)}\right), \quad (1)$$

where C is the electrical capacitance of the PZT active sensor, $Z_{str}(\omega)$ is the one-dimensional structural impedance as seen by the sensor, and $Z_A(\omega)$ is the quasi-static impedance of the sensor. At coupled-system resonance, the real part of the E/M admittance has a distinct peak. However, due to the additional stiffness contributed by the PZT wafer, the system's natural frequency may shift, although this effect diminishes greatly as the difference in size between the wafer and the structure with which it is used increases.

The E/M impedance/admittance response may be used to measure the structural dynamics of a material. Referring to FIG. 1, consider a one-dimensional structure (for example a beam) 10 upon which is attached a ceramic PZT active sensor 12 having a length $l_a$, at a position on beam 10 between $x_a$ and $x_a+l_a$. Upon activation, the PZT active sensor expands by $\gamma_{PZT}$. This generates a reaction force $F_{PZT}$ from the beam onto sensor 12 and an equal and opposite force from the sensor onto the beam. This force excites the beam. At the neutral axis, the effect is felt as an axial force excitation, $N_{PZT}$, and a bending moment excitation, $M_{PZT}$. As the active sensor is electrically excited with a high-frequency harmonic signal, it induces elastic waves into the beam structure. The elastic waves travel sideways into the beam structure, setting the beam into oscillation. In a steady-state regime, the structure oscillates at the PZT excitation frequency. The reaction force per unit displacement (dynamic stiffness) presented by the structure to the PZT depends on the internal state of the structure, on the excitation frequency, and on the boundary conditions:

$$k_{str}(\omega)=\hat{F}_{PZT}(\omega)/\hat{u}_{PZT}(\omega), \quad (2)$$

where $\hat{u}_{PZT}(\omega)$ is the displacement amplitude at frequency $\omega$, $\hat{F}_{PZT}(\omega)$ is the reaction force, and $k_{str}(\omega)$ is the dynamic stiffness. The symbol ^ signifies amplitude. Since the size of the PZT is very small with respect to the size of the structure, equation (2) represents a point-wise structural stiffness.

Consider a PZT wafer of length $l_a$, thickness $t_a$, and width $b_a$, undergoing longitudinal expansion, $u_1$, induced by the thickness polarization electric field, $E_3$. The electric field is produced by the application of a harmonic voltage $V(t)=\hat{V}e^{i\omega t}$ between the top and bottom surfaces (electrodes). The resulting electric field, $E=V/t$, is assumed uniform with $x_1$ ($\partial E/\partial x_1=0$) The length, width, and thickness are assumed to have widely separated values ($t_a \ll b_a \ll l_a$) such that the length, width, and thickness motions are practically uncoupled.

Relevant equations regarding the PZT material are:

$$S_1 = s^E_{11}T_1 + d_{31}E_3 \quad (3)$$

$$D_3 + d_{31}T_1 + \epsilon^T_{33}E_3 \quad (4)$$

where $S_1$ is the strain, $T_1$ is the stress, $D_3$ is the electrical displacement (charge per unit area), $s^E_{11}$ is the mechanical compliance at zero field, $\epsilon^T_3$ is the dielectric constant at zero stress, $d_{31}$ is the induced strain coefficient, i.e., mechanical strain per unit electric field.

Figure 2:
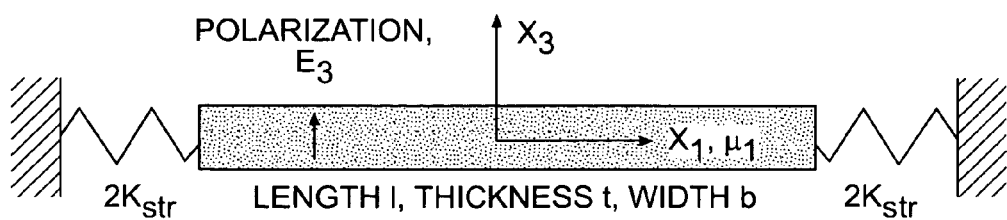
FIG. 2 is a cross-sectional diagrammatic illustration of a PZT wafer active sensor constrained by structural stiffness.

Since the piezoelectric active sensor is ultimately bonded to the structure, an elastically constrained sensor is considered. As a result of this assumption, the active sensor is constrained by structural stiffness, $k_{str}$, as shown in FIG. 2. For symmetry, the structural stiffness has been split into two end components, each of size $2k_{str}$. The boundary conditions applied at both ends connect the resultant of internal stresses with the spring reaction force, i.e., $$T_1\left(\frac{1}{2}l_a\right)b_a t_a = -2k_{str}u_1\left(\frac{1}{2}l_a\right) \quad (5)$$

$$T_1\left(-\frac{1}{2}l_a\right)b_a t_a = 2k_{str}u_1\left(-\frac{1}{2}l_a\right)$$

Substitution of Eq. (5) into Eq. (3) gives:

$$u'_1\left(\frac{1}{2}l_a\right)b_a t_a = -2k_{str}\frac{s^E_{11}}{bt}u_1\left(\frac{1}{2}l_a\right) + d_{31}E_3 \quad (6)$$

$$u'_1\left(-\frac{1}{2}l_a\right)b_a t_a = 2k_{str}\frac{s^E_{11}}{bt}u_1\left(-\frac{1}{2}l_a\right) + d_{31}E_3$$

Introducing the quasi-static stiffness of the PZT active sensor, $$k_{PZT} = \frac{A_a}{s^E_{11}l_a} \quad (7)$$

and the stiffness ratio $$r = \frac{k_{str}}{k_{PZT}} \quad (8)$$

Now Eq. (6) can be re-arranged in the form:

$$u'_1\left(\pm\frac{1}{2}l_a\right)b_a t_a \pm \frac{r}{\frac{l_a}{2}} \cdot u_1\left(\frac{1}{2}l_a\right) = d_{31}E_3 \quad (9)$$

Using Newton's law of motion, $T'_1 = \rho\ddot{u}_1$, and the strain-displacement relation, $s_1 = u'_1$, Eq. (3) yields the axial waves equation:

$$\ddot{u}_1 = c_a^2 u''_1 \quad (10)$$

where $(\dot{\ }) = \partial(\ )/\partial t$ and $(\ )' = \partial(\ )/\partial x$, while $c_a^2 = 1/\rho s_{11}^E$ is the sound speed. The general solution of Eq. (10) is:

$$u_1(x,t) = \hat{u}_1(x)e^{i\omega t} \text{ where } \hat{u}_1(x) = (C_1 \sin \gamma x + C_2 \cos \gamma x) \quad (11)$$

The variable $\gamma = \omega/ca$ is the wave number, and ( ^ ) signifies the harmonic motion amplitude. The constants $C_1$ and $C_2$ are to be determined from the boundary conditions.

Substitution of the general solution (Eq. 11) yields the following linear system in $C_1$ and $C_2$:

$$(\varphi\cos\varphi + r\sin\varphi)C_1 - (\varphi\sin\varphi - r\cos\varphi)C_2 = \frac{1}{2}u_{ISA} \quad (12)$$

$$(\varphi\cos\varphi + r\sin\varphi)C_1 + (\varphi\sin\varphi - r\cos\varphi)C_2 = \frac{1}{2}u_{ISA}$$

where $u_{ISA} = d_{31}\hat{E}_3 \cdot l_a$ and $\phi = 1;2\gamma l_a$. Upon solution, $$\hat{u}_1(x) = \frac{1}{2}u_{ISA}\frac{\sin\gamma x}{(\varphi\cos\varphi + r\sin\varphi)} \quad (13)$$

Equation (4) can be re-expressed as:

$$D_3 = \frac{d_{31}}{s^E_{11}}(u'_1 - d_{31}E_3) + \varepsilon^T_{33}E_3 = \varepsilon^T_{33}E_3\left[1 + \kappa^2_{31}\left(\frac{u'_1}{d_{31}E_3} - 1\right)\right] \quad (14)$$

where $\kappa_{13}^2 = d_{31}^2 l(s^E_{11}\epsilon_{33})$ is the E/M coupling factor. Integration of Eq. (14) yields the charge:

$$Q = \int_{-l_a/2}^{+l_a/2} \int_{-b_a/2}^{+b_a/2} D_3 \, dx \, dy = \epsilon_{33}^T \frac{b_a l_a}{t} V \left[ 1 + \kappa_{31}^2 \left( \frac{1}{l_a} \frac{1}{d_{31}E_3} u_1 \Big|_{-\frac{l_a}{2}}^{+\frac{l_a}{2}} - 1 \right) \right] \quad (15)$$

where $\epsilon^T_{33} b_a l_a / t_a = C$ is the conventional capacitance of the piezoelectric wafer. For harmonic motion, $\hat{I} = i\omega \cdot \hat{Q}$. Recalling the expressions $Y = \hat{I}/\hat{V}$ and $Z = Y^{-1}$ for the electric admittance and impedance, the admittance and impedance expressions for a PZT active sensor constrained by the structural substrate with an equivalent stiffness ratio r are:

$$Y = i\omega \cdot C \left[ 1 - \kappa_{31}^2 \left( 1 - \frac{1}{\varphi \cot \varphi + r} \right) \right] \quad (16)$$

$$Z = \frac{1}{i\omega \cdot C} \left[ 1 - \kappa_{31}^2 \left( 1 - \frac{1}{\varphi \cot \varphi + r} \right) \right]^{-1}$$

In this equation, the structural stiffness ratio, r, is additive to the sensor resonance term, $\phi \cot \phi$. When the PZT active sensor is used in a frequency sweep, the apparent structural stiffness, $k_{str}$, will vary with frequency, going through zero at structural resonances and through extreme values at structural anti-resonances. Eqs. (16) infer that both structural resonances and sensor resonances will be reflected in the admittance and impedance frequency spectra.

Analysis of the asymptotic behavior of Eqs. (16) reveals important facts. , As $r \to 0$, i.e., vibrations of a free-free sensor, $$Y_{free} = i\omega \cdot C \left[ 1 - \kappa_{31}^2 \left( 1 - \frac{1}{\varphi \cot \varphi} \right) \right].$$

As r becomes infinitely large, i.e., vibrations of a clamped sensor, $Y_{clamped} = i\omega \cdot C[1 - \kappa_{31}^2]$. On the other hand, as $\gamma la \to 0$ (i.e., quasi-static sensor conditions):

$$Y = i\omega \cdot C \left[ 1 - \kappa_{31}^2 \frac{r}{1+r} \right], \quad (17)$$

$$Z = \frac{1}{i\omega \cdot C} \left[ 1 - \kappa_{31}^2 \frac{r}{1+r} \right]^{-1}$$

The expressions contained in Eqs. (16) bridge the gap between high-frequency sensor-focused analysis and low-frequency structure-focused analysis. The present results cover the complete frequency spectrum and encompass both structure and sensor dynamics.

The effect of structural and sensor damping can be easily introduced in Eqs. (16) by the use of complex notations:

$$\bar{Y} = i\omega \cdot \bar{C} \left[ 1 - \bar{\kappa}_{31}^2 \left( 1 - \frac{1}{\bar{\varphi} \cot \bar{\varphi} + \bar{r}} \right) \right] \quad (18)$$

$$\bar{Z} = \frac{1}{i\omega \cdot \bar{C}} \left[ 1 - \bar{\kappa}_{31}^2 \left( 1 - \frac{1}{\bar{\varphi} \cot \bar{\varphi} + \bar{r}} \right) \right]^{-1}$$

where $\bar{r}$ is the frequency-dependent complex stiffness ratio that reflects the structural point-wise dynamics and the sensor dissipation mechanisms.

The response of the structural substrate to the PZT excitation is deduced from the general theory of beam vibrations. The excitation forces and moments acting upon the beam structure are derived from the PZT force, $F_{PZT} = \hat{F}_{PZT} e^{i\omega t}$, using the beam cross-section geometry:

$$M_a = F_{PZT} \frac{h}{2}, \quad N_a = F_{PZT} \quad (19)$$

The space-wise distribution of excitation bending moment and axial force are expressed using the Heaviside function, $H(x-x_a)$, defined as $H(x-x_a) = 0$ for $x < x_a$, and $H(x-x_a) = 1$ for $x_a \leq x$:

$$N_e(x,t) = N_a[-H(x-x_a) + H(x-x_a-l_a)] \cdot e^{i\omega t} \quad (20)$$

$$M_e(x,t) = M_a[-H(x-x_a) + H(x-x_a-l_a)] \cdot e^{i\omega t} \quad (21)$$

Equations (20) and (21) correspond to axial and flexural vibrations, respectively. Axial vibrations modes are usually of much larger frequency than flexural vibration modes, but their vibration frequencies are commensurable with those of the PZT active sensors. Thus, both axial and flexural vibrations are considered.

The equation of motion for axial vibrations is:

$$\rho A \cdot \ddot{u}(x,t) - EA \cdot u''(x,t) = N'_e(x,t) \quad (22)$$

Assume modal expansion $$u(x,t) = \sum_{n=0}^{\infty} C_n X_n(x) \cdot e^{i\omega t} \quad (23)$$

where $X_n(x)$ are orthonormal mode shapes, i.e., $\int X_m X_n dx = \delta_{mn}$, with $\delta_{mn} = 1$ for $m = n$, and 0 otherwise. $C_n$ are the modal amplitudes. Substitution of Eq. (20) into (22) yields:

$$\rho A \cdot \ddot{u}(x,t) - EA \cdot u''(x,t) = \hat{N}_a[-\delta(x-x_a) + \delta(x-x_a-l_a)] \cdot e^{i\omega t} \quad (24)$$

where $\delta$ is Dirac's function. Since the mode shapes satisfy the free-vibration differential equation $EA \cdot X''_n + \omega^2_n \rho A \cdot X_n = 0$, multiplication by $X_n(x)$ and integration over the length of the beam yields:

$$C_n = \frac{1}{\omega_n^2 - \omega^2} \cdot \frac{\hat{N}_a}{\rho A} [-X(x_a) + X(x_a + l_a)] \quad (25)$$

Hence, $$u(x,t) = \frac{\hat{N}_a}{\rho A} \sum_{n=0}^{\infty} \frac{-X_n(x_a) + X_n(x_a + l_a)}{\omega_n^2 - \omega^2} \cdot X_n(x) \cdot e^{i\omega t} \quad (26)$$

For Euler-Bernoulli beams, the equation of motion under moment excitation is:

$$\rho A \cdot \ddot{w}(x,t) - EI \, w''''(x,t) = -M''_e(x,t) \quad (27)$$

Substitution of Eq. (21) into (27) yields:

$$\rho A \cdot \ddot{w}(x,t) + EI \cdot w''''(x,t) = \hat{M}_a[-\delta'(x-x_a) + \delta'(x-x_a-l_a)] \cdot e^{i\omega t} \quad (28)$$

where $\delta'$ is the first derivative of Dirac's function ($\delta'$=H'')

Assume modal expansion $$w(x,t) = \sum_{n=N_1}^{N_2} C_n X_n(x) \cdot e^{i\omega t},$$

where $X(x)$ are the orthonormal bending mode shapes, and $N_1$, $N_2$ are the mode numbers enduring the frequency band of interest. Since the mode shapes satisfy the free-vibration differential equation $EI \cdot X_n'''' = \omega^2_n \cdot \rho A \cdot X_n$, multiplication by $X_n(x)$ and integration over the length of the beam yields:

$$C_n = \frac{1}{\omega_n^2 - \omega^2} \cdot \frac{\hat{M}_a}{\rho A} \int_0^l X_n(x)[\delta'(x-x_a) - \delta'(x-x_a-l_a)] dx \quad (29)$$

Integration by parts and substitution into the modal expansion expression yields:

$$C_n = -\frac{1}{(\omega_n^2 - \omega^2)} \frac{\hat{M}_a}{\rho A}[-X_n'(x_a) + X_n'(x_a+l_a)] \quad (30)$$

Hence, $$w(x,t) = -\frac{\hat{M}_a}{\rho A}\sum_{n=1}^{\infty} \frac{-X_n'(x_a) + X_n'(x_a+l_a)}{\omega_n^2 - \omega^2} \cdot e^{i\omega t} \quad (31)$$

To obtain the dynamic structural stiffness, $k_{str}$, presented by the structure to the PZT, the elongation between the two points, A and B, connected to the PZT ends is first calculated. Simple kinematics gives the horizontal displacement of a generic point P placed on the surface of the beam:

$$u_P(t) = u(x) - \frac{h}{2}w'(x), \quad (32)$$

where u and w are the axial and bending displacements of the neutral axis. Letting P be A and B, and taking the difference, yields:

$$u_{PZT}(t) = u_B(t) - u_A(t) = u(x_a,t) - u(x_a+l_a,t) - h/2[w'(x_a,t) - w'(x_a+l_a,t)] \quad (33)$$

Using Eqs. (19), (26), and (31), the amplitude of Eq. (33) becomes $$\hat{u}_{PZT} = \frac{\hat{F}_{PZT}}{\rho A}\left\{\sum_{n_u}\frac{[U_{n_u}(x_a+l_a) - U_{n_u}(x_a)]^2}{\omega_{n_u}^2 - \omega^2} + \left(\frac{h}{2}\right)^2\sum_{n_u}\frac{[W'_{n_u}(x_a+l_a) - W'_{n_u}(x_a)]^2}{\omega_{n_u}^2 - \omega^2}\right\} \quad (34)$$

where differentiation between axial and flexural vibrations frequencies and mode shapes was achieved by the use of $n_u$, $\omega_{n_u}$, $U_{n_u}(x)$ and $n_w$, $\omega_{n_k}$, $W_{n_w}(x)$, respectively. Dividing Eq. (34) by $\hat{F}_{PZT}$ yields the structural frequency response function (FRF) to the Single Input Single Output (SISO) excitation applied by the PZT active sensor. This situation is similar to conventional modal testing with the proviso that the PZT wafers are unobtrusive and permanently attached to the structure. For convenience, the axial and flexural components of the structural FRF are expressed separately, i.e., $$H_u(\omega) = \frac{1}{\rho A}\sum_{n_u}\frac{[U_{n_u}(x_a+l_a) - U_{n_u}(x_a)]^2}{\omega_{n_u}^2 + 2i\zeta_{n_u} - \omega^2}, \quad (35)$$

$$H_w(\omega) = \frac{1}{\rho A}\left(\frac{h}{2}\right)^2\sum_{n_w}\frac{[W'_{n_u}(x_a+l_a) - W'_{n_u}(x_a)]^2}{\omega_{n_u}^2 + 2i\zeta_{n_u} - \omega^2} \quad (36)$$

Modal damping, $\zeta$, was introduced to provide practical veridicality to the model. The FRF's are additive, and the total FRF is simply $$H(\omega) = H_u(\omega) + H_w(\omega) \quad (37)$$

The SISO FRF is the same as the dynamic structural compliance, as seen by the PZT wafer active sensor. The dynamic structural stiffness is the inverse of the structural compliance, i.e., $$k_{str}(\omega) = \frac{\hat{F}_{PZT}}{\hat{u}_{PZT}} = \rho A\left\{\sum_{n_u}\frac{[U_{n_u}(x_a+l_a) - U_{n_u}(x_a)]^2}{\omega_{n_u}^2 + 2i\zeta_{n_u} - \omega^2} + \left(\frac{h}{2}\right)^2\sum_{n_u}\frac{[W'_{n_u}(x_a+l_a) - W'_{n_u}(x_a)]^2}{\omega_{n_u}^2 2i\zeta_{n_u} - \omega^2}\right\}^{-1} \quad (38)$$

For free-free beams axial and flexural components [31]:

$$U_{n_u}(x) = A_{n_u}\cos(\gamma_{n_u}x), \; A_{n_u} = \sqrt{2/l}, \qquad (39)$$

$$\gamma_{n_u} = \frac{n_u\pi}{l}, \; \omega_{n_u} = \gamma_{n_u}c, \; c = \sqrt{\frac{E}{\rho}}, \; n_u = 1, 2, \ldots$$

$$W_{n_w}(x) = \qquad (40)$$

$$A_{n_u}[\cosh\gamma_{n_u}x + \cos\gamma_{n_w}x - \sigma_{n_u}(\sinh\gamma_{n_w}x + \sin\gamma_{n_u}x)]\omega_{n_u} = \gamma_{n_u}^2 a,$$

$$a = \sqrt{\frac{EI}{\rho A}}, \; A_{nw} = 1 \bigg/ \sqrt{\int_0^l W_{n_u}^2(x)dx}.$$

Numerical values of $l\cdot\gamma_{n_k}$ and $\sigma_{n_w}$ for $n_w \leq 5$ can be found in Blevins, R. D., (1979) "Formulas for Natural Frequency and Mode Shape," page 108, Litton Educational Publishing Inc.; for $5 < n_w$, $$\gamma_{n_w} = \frac{1}{l}\frac{(2n+1)\pi}{2} \; \text{and} \; \sigma_{n_w} = 1.$$

Experimental Results

The analytical model described above was used to perform several numerical simulations that directly predict the E/M impedance and admittance signature at an active sensor's terminals during structural identification. Subsequently, 1X experiments were performed to verify these predictions The simulation conditions identically represent specimens consisting of small steel beams (E=200GPa, $\rho$=7750 kg/m$^3$) of various thicknesses and widths. All beams were 100 mm long with various widths, $b_1$=8 mm (narrow beams) and $b_2$=19.6 mm (wide beams). The nominal thickness of the specimen was $h_1$=2.6 mm. Double thickness specimens, $h_2$=5.2 mm, were created by gluing two specimens back-to-back. Thus, four beam types were used: narrow-thin, narrow-thick, wide-thin, and wide-thick. The comparison of wide and narrow beams was aimed at identifying the width effects in the frequency spectrum, while the change from double to single thickness was aimed at simulating the effect of corrosion (for traditional structures) and disbonding/delamination of adhesively bonded and composite structures. All specimens were instrumented with thin 7 mm square PZT active sensors (l=7 mm, b=7 mm, and t=0.22 mm) placed at $x_a$=40 mm from one end.

The numerical simulation was performed using a MATHCAD-coded simulation based on modal analysis theory, assuming a damping coefficient of 1% for steel beams. Numerically exact expressions for the axial and flexural frequencies and mode shapes were used. The simulation was performed over a modal subspace that incorporates all modal frequencies in the frequency bandwidth of interest. The theoretical analysis indicates that these frequencies should be identical with the basic beam resonances. The "calc" columns of Table 1 show the first six predicted resonances for axial and flexural vibrations. During the experiments, a Hewlett-Packard 4194A Impedance Analyzer was used to record the E/M impedance real part spectrum in the 1–30 kHz range. To approximate the free-free boundary conditions, the beams were supported on common packing foam. The beam natural frequencies were identified from the E/M impedance spectrum. The results are given in the "EXP" columns of Table 1. When the beam thickness was doubled, the frequencies also doubled. This is consistent with theoretical prediction. The error between theory and experiment, however, seems larger for the double thickness beam.

The experimental results indicate frequency clusters, which move to higher frequencies as beam width is reduced. The frequency clusters appear to be associated with width vibrations. Width vibrations are also influenced by thickness, i.e., they shift to higher frequencies as thickness increases. This is also noticeable in Table 1, which shows that the lowest cluster appeared for the single-thickness wide specimen and that the highest cluster appeared for double-thickness narrow beam.

For purposes of comparison, dynamic identification was also X attempted with conventional modal analysis methods. A small steel beam with dimensions identical to the "narrow thin" specimen in Table 1 was instrumented with two CEA-13-240UZ-120 strain gauges connected in half bridge configuration to a P-3500 strain indicator available from Measurements Group, Inc. The specimen was suspended in a free-free configuration and excited with a sharp impact. The resulting signal was collected with an HP 54601B digital oscilloscope and numerically processed on a personal computer. Standard signal analysis algorithms (FFT) were used to extract the frequency spectrum. The first natural frequency (1.387 kHz) was clearly displayed. The second natural frequency (3.789 kHz) could also be identified but with a much weaker amplitude. These results were consistent with theoretical values and the experimental results presented in Table 1, but the impact excitation method was not able to excite other higher frequencies depicted in Table 1, most probably due to bandwidth limitations.

In order to obtain consistent experimental results, a set of sensors was subject to a calibration procedure consisting of geometrical and electrical measurements and measurements of the intrinsic E/M impedance and admittance spectra of the PZT active sensors. The results show small dimension variations from sensor to sensor. The mean and standard deviation values for length/width and thickness were 6.95 mm, +/−0.5%, and 0.224 mm, +/−1.4%, respectively. Electrical capacitance was measured on an in-process quality check to be applied during each step of sensor development and during the sensor installation process. Mean and standard deviation values were 3.276 mF, +/−3.8%.

The intrinsic E/M impedance and admittance spectra of the PZT active sensors, before being attached to the structure, were measured with an HP 4194A Impedance Phase-Gain Analyzer. The PZT wafer was centered on a bold head and held in place with a probe tip. Thus, center clamping conditions were simulated, and the wafer could perform free vibrations while being tested. Mean values of 251 kHz and standard deviations of +/−0.2% were obtained.

TABLE 1

Theoretical and experimental results for wide and
narrow beams with single and double thickness

| | Beam #1 (narrow thin) | | | Beam #2 (Narrow thick) | | | Beam #3 (wide thin) | | | Beam #4 (wide thick) | | |
|---|---|---|---|---|---|---|---|---|---|---|---|---|
| # | Calc. KHz | Exp. kHz | Δ % | Calc. kHz | Exp. kHz | Δ % | Calc. kHz | Exp. KHz | Δ % | Calc. kHz | Exp. kHz | Δ % |
| 1 | 1.396 | 1.390 | −0.4 | 2.847 | 2.812 | −1.2 | 1.390 | 1.363 | −1.9 | 2.790 | 2.777 | −0.5 |
| 2 | 3.850 | 3.795 | −1.4 | 7.847 | 7.453 | −5.2 | 3.831 | 3.755 | −2 | 7.689 | 7.435 | −3.4 |
| 3 | 7.547 | 7.4025 | −2 | 15.383 | 13.905 | −10.6 | 7.510 | 7.380 | −1.7 | 15.074 | 13.925 | −8.2 |
| 4 | 12.475 | 12.140 | −2.7 | | 29.650 | | 12.414 | 12.093 | −2.6 | | 21.825 | |
| 5 | 18.635 | 17.980 | −3.6 | 25.430 | 21.787 | −16.7 | 18.545 | 17.965 | −3.2 | 24.918 | 22.163 | −12.4 |
| 6 | | 24.840 | | | | | | 24.852 | | | | |
| 7 | 26.035 | 26.317 Cluster 175 kHz | 1 | 26.035 | 26.157 Cluster 210 kHz | 0.5 | 26.022 | 26.085 Cluster 35 kHz | 0.2 | 25.944 | 26.100 Cluster 60 kHz | 0.6 |

The active sensors used in the experiments were very small and therefore did not significantly disturb the dynamic properties of the structure under consideration. Table 2 presents the mass and stiffness for the sensor and structure. For purposes of comparison, the table also presents the mass of an accelerometer.

TABLE 2

Numerical illustration of the non-invasive
properties of the piezoelectric wafer active sensors

| Sensor type | Mass, g | % of structural mass | Stiffness, MN/m | % of structural stiffness |
|---|---|---|---|---|
| Active sensor | 0.082 | 0.5% | 15 | 1.5% |
| Structure | 16.4 | N/A | 1000 | N/A |
| Accelerometer: 352A10, PCB Piezotronics | 0.7 | 4.3% | N/A | N/A |

Table 2 illustrates the non-invasive properties of piezoelectric wafer active sensors. The mass and stiffness editions of the sensors are within about 1% (0.5% for mass, and 1.5% for stiffness).

Figure 3:
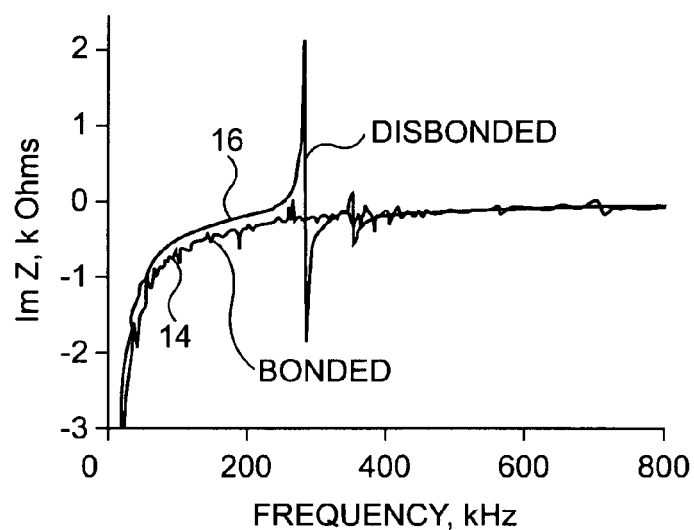
FIG. 3 is a graphical representation of a self-diagnostic performed in a sensor in accordance with an embodiment of the present invention.

As described in more detail above, the present invention contemplates embedding piezoelectric wafer transducers on mechanical structures for potentially long periods of time. Thus, it is desirable to intermittently monitor the integrity of a transducer or transducer array. Accordingly, a self-diagnostic may be employed in which the reactive part of the transducer's impedance is measured over a relatively broad frequency range. Piezoelectric active sensors are predominately capacitive devices dominated by reactive impedance. Baseline impedance signatures can be used to identify defective active sensors. Referring to FIG. 3, for example, a reactive impedance spectrum 14 of a well-bonded PZT sensor is compared with an impedance spectrum 16 of a disbanded (free) sensor. The appearance of sensor free-vibration resonance and the disappearance of structural resonances provide un-ambiguous features that indicate the degree of the transducer's integrity.

Figure 4:
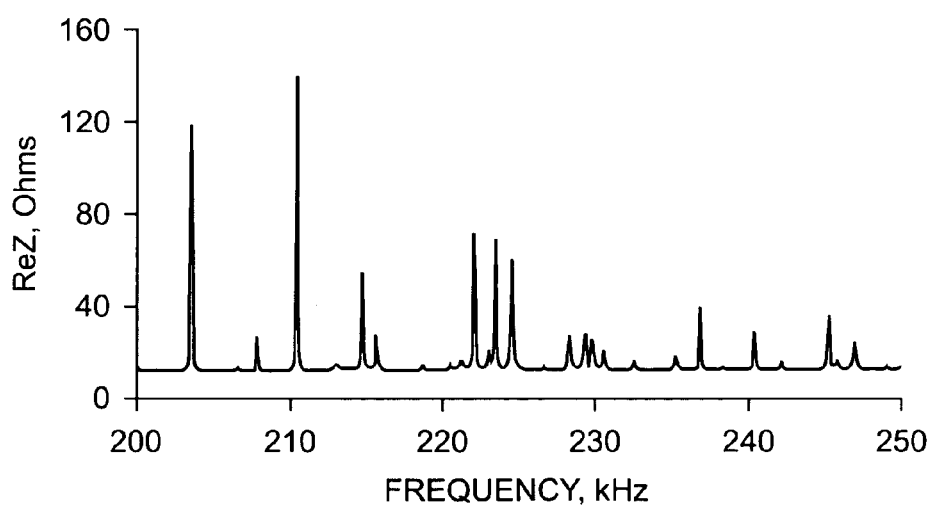
FIG. 4 is a graphical representation of an impedance spectrum measured by a sensor array in accordance with an embodiment of the present invention.

Piezoelectric active sensors, and the associated structural dynamic identification method described above based on electro-mechanical impedance response, is well-suited for small rigid machinery parts having natural frequencies in the kHz range. For example, FIG. 4 illustrates the natural frequencies identified by two PZT active sensors disposed on an aircraft turbo-engine blade, one on the blade's main portion and one at the blade root. Following identification of such impedance spectra from the sensors, the sensors may thereafter be periodically monitored for deviations in the spectra that could indicate structural defects in the blade.

What is claimed is:

1. A system operative to detect a damage feature in a thin wall structure, said system comprising:
    an array of piezoelectric wafer sensors embedded on said structure in a predetermined pattern;
    a generator operative to excite at least one of said sensors to produce tuned ultrasonic guided waves having a frequency of at least about 200 KHz in said structure; and
    a signal processor operative to process received signals reflected from said damage feature at said at least one sensor so as to detect said damage feature via a pulse-echo technique.

2. A system as set forth in claim 1, wherein said frequency of said ultrasonic waves include a significant component at approximately 300 KHz.

3. A system as set forth in claim 2, wherein said ultrasonic waves are Lamb waves.

4. A system as set forth in claim 1, wherein said frequency of said ultrasonic waves falls in the megahertz range.

5. A system as set forth in claim 1, wherein said ultrasonic waves are Lamb waves.

6. A system as set forth in claim 5, wherein said sensors are adhered to a surface of said thin wall structure.

7. A system as set forth in claim 1, wherein said wafer sensors have a planar surface area no greater than approximately 169 mm$^2$ and a thickness no greater than approximately 0.49 mm.

8. A system as set forth in claim 7, wherein said wafer sensors are generally rectangular.

9. A system operative to detect a damage feature in a thin wall structure, said system comprising:
    an array of piezoelectric wafer sensors embedded on said structure in a predetermined pattern;
    a generator operative to excite at least one of said sensors to produce ultrasonic waves having a frequency of at least about 200 KHz in said structure, said generator being operative to excite each of said sensors in said array in round-robin fashion; and
    a signal processor operative to process received signals at least two of said sensors so as to detect said damage feature.

10. A system as set forth in claim 9, wherein said signal processor is operative to determine a location of said damage feature based on a collection of data representing received signals at a plurality of said sensors after round-robin excitation of all of said sensors in said array.

11. A system as set forth in claim 9, wherein said array comprises at least four of said sensors.

12. A system operative to detect a damage feature in a structure, said system comprising:
   an array of piezoelectric wafer active sensors embedded on said structure in a predetermined pattern, said wafer sensors having a planar surface area no greater than approximately 169 mm$^2$ and a thickness no greater than approximately 0.49 mm;
   a generator operative to excite each of sensors in said array in round-robin fashion to produce ultrasonic waves in said structure; and
   a signal processor operative to process received signals at least two of said sensors so as to detect said damage feature.

13. A system as set forth in claim 12, wherein said signal processor is operative to determine a location of said damage feature based on a collection of data representing received signals at a plurality of said sensors after round-robin excitation of all of said sensors in said array.

14. A system as set forth in claim 12, wherein said array comprises at least four of said sensors.

15. A system as set forth in claim 12, wherein said frequency of said ultrasonic waves falls in a range of 200 kHz to high megahertz.

16. A system as set forth in claim 12, wherein said frequency of said ultrasonic waves is approximately 300 KHz.

17. A system as set forth in claim 16, wherein said ultrasonic waves are Lamb waves.

18. A system as set forth in claim 12, wherein said sensors are adhered to a surface of said thin wall structure.

19. A method of detecting a damage feature present within a predetermined sensing zone in a thin wall structure, said method comprising steps of:
   (a) providing at least one piezoelectric wafer sensor embedded on said structure;
   (b) exciting said sensor with a first electrical signal spanning a predetermined frequency range;
   (c) deriving first data characteristic of a drive-point impedance of said wafer sensor as embedded on said structure;
   (d) exciting said sensor with a second electrical signal spanning said predetermined frequency range;
   (e) deriving second data characteristic of said drive-point impedance of said wafer sensor; and
   (f) comparing said first data and said second data.

20. A method as set forth in claim 19, wherein a plurality of said wafer sensors are provided on said structure in an array.

21. A method as set forth in claim 20, wherein said sensors are arranged in said array so as to have overlapping sensing zones.

22. A method as set forth in claim 21, wherein said wafer sensors have a planar surface area no greater than approximately 169 mm$^2$ and a thickness no greater than approximately 0.49 mm.

* * * * *